United States Patent
Levendowski et al.

[11] Patent Number: 6,161,030
[45] Date of Patent: Dec. 12, 2000

[54] PORTABLE EEG ELECTRODE LOCATOR HEADGEAR

[75] Inventors: Daniel J. Levendowski; Christine Berka; Zoran R. Konstantinovic, all of Los Angeles, Calif.

[73] Assignee: Advanced Brain Monitoring, Inc., Carlsbad, Calif.

[21] Appl. No.: 09/245,784

[22] Filed: Feb. 5, 1999

[51] Int. Cl.[7] .................................................. A61B 5/0478
[52] U.S. Cl. ........................... 600/383; 600/393; 607/139
[58] Field of Search .................................... 600/383, 390, 600/393; 607/544, 139

[56] References Cited

U.S. PATENT DOCUMENTS

| | | |
|---|---|---|
| 3,490,439 | 1/1970 | Rolston .................................... 600/383 |
| 3,998,213 | 12/1976 | Price . |
| 4,537,198 | 8/1985 | Corbett . |
| 4,709,702 | 12/1987 | Sherwin . |
| 4,770,180 | 9/1988 | Schmidt et al. . |
| 4,836,219 | 6/1989 | Hobson et al. . |
| 4,967,038 | 10/1990 | Gevins et al. . |
| 5,038,782 | 8/1991 | Gevins et al. . |
| 5,273,037 | 12/1993 | Itil et al. . |
| 5,291,888 | 3/1994 | Tucker . |
| 5,293,867 | 3/1994 | Oommen ................................. 600/383 |
| 5,348,006 | 9/1994 | Tucker . |
| 5,357,957 | 10/1994 | Itil et al. . |
| 5,404,875 | 4/1995 | Gevins et al. . |
| 5,479,934 | 1/1996 | Imran . |
| 5,564,433 | 10/1996 | Thornton . |
| 5,800,351 | 9/1998 | Mann ....................................... 600/383 |

OTHER PUBLICATIONS

Article entitled "A Dry Electrode For EEG Recording," B. Taheri, R. Knight and R. Smith, 1994 Elsevier Science Ireland Ltd., pp. 2–9.

Primary Examiner—Lee Cohen
Attorney, Agent, or Firm—Fulwider Patton Lee & Utecht, LLP

[57] ABSTRACT

The EEG electrode locator headgear allows the user to locate and apply disposable EEG electrodes accurately according to the International 10/20 System without technical assistance, to allow the acquisition of high quality EEG signals. The headgear includes a front forehead pad, a base strap assembly connected to the front forehead pad, a plurality of EEG electrode locators for receiving EEG electrodes, and a plurality of locator straps connected to the front pad of material, the base strap assembly, and to the plurality of EEG electrode locators for accurately positioning the plurality of EEG electrode locators positioned relative to the scalp of a user. A visor can be attached to the front pad of material, and the base strap assembly may include an occipital locator device. A plunger assembly with spreadable fingers for parting the hair of the scalp of the user is also provided that is inserted in the electrode locators to prepare the scalp of the user and to seat the electrodes.

46 Claims, 5 Drawing Sheets

PORTABLE EEG ELECTRODE LOCATOR HEADGEAR

The United States Government has rights to this invention pursuant to research supported in whole or in part by NIH contracts R43NS6344 and N43NS72367 and grant R43NS35387 awarded by the National Institute of Neurological Disease and Stroke.

BACKGROUND OF THE INVENTION

1. Field of the Invention

This invention relates generally to devices for the acquisition of electroencephalographic (EEG) signals, and more particularly concerns an electrode locator device that can be applied by a user without assistance for acquiring high quality EEG signals, and is comfortable and cosmetically acceptable for use during daily activities.

2. Description of Related Art

Advances in detection and characterization of electroencephalographic (EEG) signals from the brain have allowed EEG monitoring to be useful in analysis of neurological disorders, and laboratory studies of awareness and sleep. Recent advances have, for example, provided much information about the correlation between EEG signals and an individual's level of arousal, in a continuum from vigilance to drowsiness, and sleep onset. Devices for monitoring EEG signals are typically used in a laboratory environment or in a home for sleep studies, but are typically set up and operated by trained technicians. Shifts in EEG signals have been directly correlated with changes in performance, particularly during tasks which require sustained attention over prolonged periods of time. However, application of EEG monitoring to environments for study and monitoring of brain performance, such as for monitoring brain activity in the home, office, aircraft cockpit, and train or truck operations cabins, for example, has been severely hampered by cumbersome detection and recording equipment, and the need for the assistance of a technician typically required to obtain high quality data.

In fitting EEG electrodes to the scalp of a subject being monitored, an EEG technician will typically first measure the distances between the nasium and the occipital bone, and between the mastoid processes, to identify the top center (Cz) of the head, and will then position all other electrodes relative to these landmarks to comply with the International 10/20 System that is well known in the art as the standard for positioning of EEG electrodes. The technician will then part the hair of the scalp of the subject at the intended electrode sites, clean the electrode sites to remove dirt, hair oil, and the like, and prepare the scalp to remove the top layer of dead skin, to ensure that low scalp-electrode impedance values are obtained.

Conventionally, after preparation of the intended electrode sites on the scalp, electrodes are glued to the scalp with collodion, typically a viscous solution of pyroxilin, a commercially available nitrocellulose, in ether and alcohol, that is a particularly noxious preparation that can bond with the scalp and hair, to provide a stable scalp-electrode interface, until dissolved by a solvent such as acetone, or a non-acetone, oil based collodion remover.

A variety of hats, caps, helmets and headgear are known that have been developed to position EEG electrodes according to the International 10/20 System and provide a scalp-electrode interface without the use of an adhesive such as collodion. However, these types of devices are commonly uncomfortable and unacceptable for use during activities of work and daily living. One such sleep monitoring headgear utilizes a circumferential elastic headband to generate an electrode seating pressure for a single electrode located at the top center of the head of a subject. It has been found, however, that when such a circumferential elastic headband is utilized to seat multiple electrodes, the headband slides up and posteriorly on the forehead.

Such conventional hats, caps, helmets and headgear also typically make it difficult for a user to part the hair or abrade their scalp at the electrode site without assistance. Particularly where disposable electrodes are used that are not to be bonded to the scalp of the user to provide an electrode-scalp interface, the placement of an electrode over hair can increase the impedance between the electrode and scalp, causing significant signal artifacts if the hair slides or is pulled across the surface of the electrode while signals are being acquired. One such conventional device requires the technician to lift or turn a disposable electrode on its side after a conductive gel on the electrode has made contact with the hair of the scalp, in order to part the hair at the intended area of the scalp for placement of the electrode. Several systems used in the laboratory for non-ambulatory EEG monitoring dispense electrode gel to the electrode, but would make an EEG electrode locator headgear uncomfortably heavy and inconvenient for ambulatory use outside a laboratory environment. Another type of device utilizes sharp tipped metal points to penetrate the dead layer of skin. However, such sharp metal points can pose a medical danger due to the potential for infection, particularly with repeated abrasions, and the possibility of penetration of the skull if the device were to be struck accidentally during ambulatory activity, or other activities during daily living.

It would therefore be desirable to provide an EEG electrode locator headgear that utilizes electrode locators to identify electrode sites, and gives the user access for application of electrodes to the electrode sites, permitting conventional scalp preparation techniques, such as application of abrasion cream with a"Q-tip", for example, to be applied by the user without technical assistance. It would also be desirable to provide an EEG electrode locator headgear utilizing a device allowing for a user to prepare an intended electrode site on the scalp by parting of the hair, prior to seating of the electrodes, and for placement of electrodes. While prior EEG electrode locating techniques typically required a technician to accurately locate electrodes, it would be desirable to provide an EEG electrode locator headgear that utilizes a locating device that can be positioned by the user over a prominent location on the scalp of the user, such as over the occipital bone, or over the nasium, to orient the headgear and confirm accurate placement of the EEG electrodes. The present invention meets these needs.

SUMMARY OF THE INVENTION

Briefly, and in general terms, the present invention provides for an EEG electrode locator headgear for a user that allows the user to locate and apply disposable EEG electrodes accurately according to the International 10/20 System without technical assistance, to allow the acquisition of high quality EEG signals. The EEG electrode locator headgear is portable and comfortable, allowing it to be worn by the user during daily activities as one would a cap or visor. The headgear provides a stable electrode-scalp interface for a plurality of electrodes without covering the entire head, and without requiring a chin strap for normal adult usage, and allows the hair to be parted and the scalp to be prepared by the user without technical assistance.

The invention accordingly provides for an electroencephalograph (EEG) electrode locator headgear including a front pad of material having first and second ends, the front pad of material being adapted to extend across a user's forehead, a base strap assembly having a first end connected to the first end of the front pad of material, and a second end connected to the second end of the front pad of material, the front pad of material and the base strap assembly being adapted to be secured comfortably around the circumference of a user's head, a plurality of EEG electrode locators adapted to receive EEG electrodes, and a plurality of locator straps connected to the front pad of material, the base strap assembly, and to the plurality of EEG electrode locators for accurately positioning the plurality of EEG electrode locators positioned relative to the scalp of a user.

In a presently preferred embodiment, the front pad of material includes a visor attached to the front pad of material, which is typically non-elastic. The base strap assembly is preferably adjustable, and in a presently preferred aspect comprises a pair of adjustable elastic straps connected at one end to the front pad of material and adjustably connected together at the other end. The base strap may also advantageously include an occipital locator device adapted to be seated on a region of the user's scalp over the user's occipital bone, with the base strap assembly including first and second elastic edge straps connected at one end to the front pad of material, and adjustably connected at the other end to the occipital locator device. The occipital locator device preferably has a plurality of feet adapted to be positioned over the user's occipital bone. In an alternative preferred embodiment, an anterior locator strap having a free end adapted to be positioned over the user's nasium can be connected to the front pad of material, to allow the user to confirm accurate placement of the electrode locators.

In another presently preferred aspect of the invention, the EEG electrode locators each comprise a hollow tubular base adapted to receive an EEG electrode, and an annular flange extending from an upper edge of the hollow tubular base, with the annular flange including a plurality of slots for receiving a plurality of the locator straps. In another presently preferred aspect, the hollow tubular base includes an EEG electrode locator electrical conductor adapted to be electrically connected to an EEG electrode inserted in the hollow tubular base of the EEG electrode locator, and intermediate electrical conductors are electrically connected to the EEG electrode locator electrical conductors and are adapted to be connected to an EEG monitor. In a presently preferred embodiment, three EEG electrode locators are provided, adapted to be positioned at a central (Cz) position, a parietal (Pz) position, and an occipital (Oz) position, relative to the scalp of a user. Alternatively, additional electrode locators may be provided for positioning additional electrodes according to the International 10/20 system.

In another presently preferred aspect of the invention, the plurality of locator straps are made of elastic material, such that the locator straps bias the plurality of EEG electrode locators, and thereby the electrodes inserted into the electrode locators, with a biasing pressure toward the user's scalp, to provide a stable electrode-scalp interface capable of producing a high signal quality. A plurality of electrodes are also provided that are adapted to be seated in the plurality of electrode locators, respectively. As noted above, at least three electrodes are provided, although the electrode headgear can be adapted to accept more or fewer than three EEG electrodes, as desired. The electrodes are preferably disposable.

A plunger assembly is also preferably provided that is adapted to cooperate with the plurality of electrode locators either prior to or in conjunction with insertion of the EEG electrodes. The plunger assembly includes a hollow tubular base having an upper portion and a lower portion, and a plunger adapted to be received in the hollow tubular base. The plunger assembly is adapted to be inserted in the electrode locators to prepare the scalp of the user and to seat the electrodes.

The lower portion of the hollow tubular base advantageously includes a plurality of flexible, resilient fingers having distal ends that are biased to meet at a common distal central location, and that can be spread in order to part the hair of the scalp of the user at a desired site on the scalp of the user in preparation of the site for receiving an EEG electrode. The flexible, resilient fingers on the hollow tubular base of the plunger assembly are presently preferably plastic. The distal flexible, resilient fingers of the plunger hollow tubular base can be spread by insertion of an electrode through the plunger hollow tubular base, so that the plunger assembly can be used to simultaneously part the hair by spreading of the distal fingers of the plunger hollow tubular base, seat the disposable electrode, and optionally also abrade the scalp of the user at the intended location of the electrode, such as by manually twisting the hollow tubular base to rub the distal ends of the distal fingers against the scalp of the user. The plunger is adapted to be inserted in the hollow tubular base of the plunger assembly to spread the distal flexible, resilient fingers.

In one presently preferred alternate embodiment, the plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted. In another presently preferred aspect, the hollow tubular base of the plunger assembly includes an electrical conductor adapted to be electrically connected between an electrode inserted in the hollow tubular base and one of the electrode locators for conducting EEG signals from the electrodes to an EEG monitor.

These and other aspects and advantages of the invention will become apparent from the following detailed description and the accompanying drawings, which illustrate by way of example the features of the invention.

DETAILED DESCRIPTION OF THE PREFERRED EMBODIMENTS

The application of EEG monitoring to common daily environments for study and monitoring of brain performance during the normal course of daily activities has been severely hampered by cumbersome detection and recording equipment, and the need for the assistance of a technician to set up and monitor the acquisition of data in order to obtain high quality data. Simply parting the hair of the scalp and preparation of the desired portions of the scalp of a subject for proper placement of electrodes has commonly required the assistance of a technician. Particularly when disposable electrodes are to be applied by a user that are not bonded to the scalp of the user to provide an electrode-scalp interface, the proper preparation and placement of an electrode over hair can be critical for obtaining high quality signal data.

Figure 1:
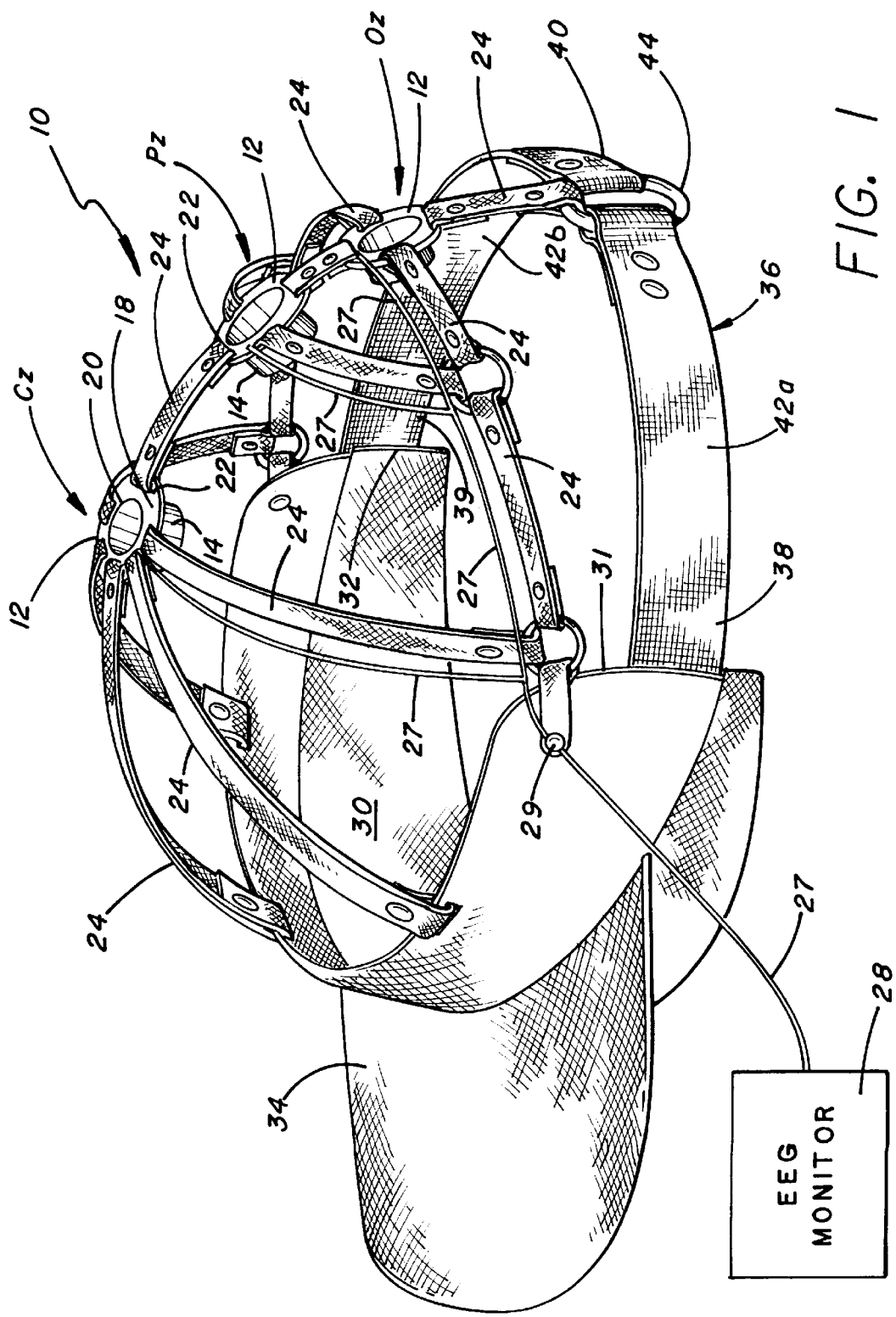
FIG. 1 is a top perspective view of a preferred embodiment of the EEG electrode locator headgear of the present invention.
Figure 4:
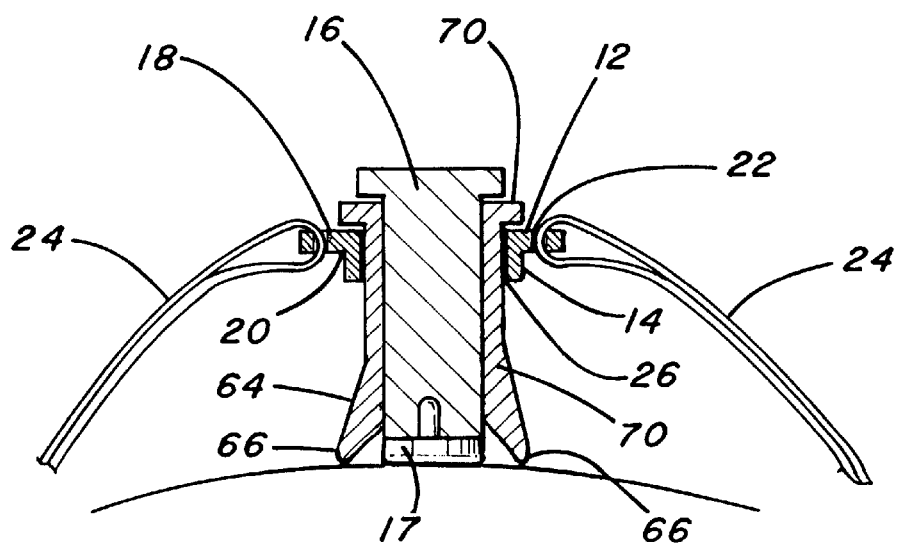
FIG. 4 is a cross-sectional view of the EEG electrode fully inserted in the plunger assembly and electrode locator of FIG. 3.
Figure 6:
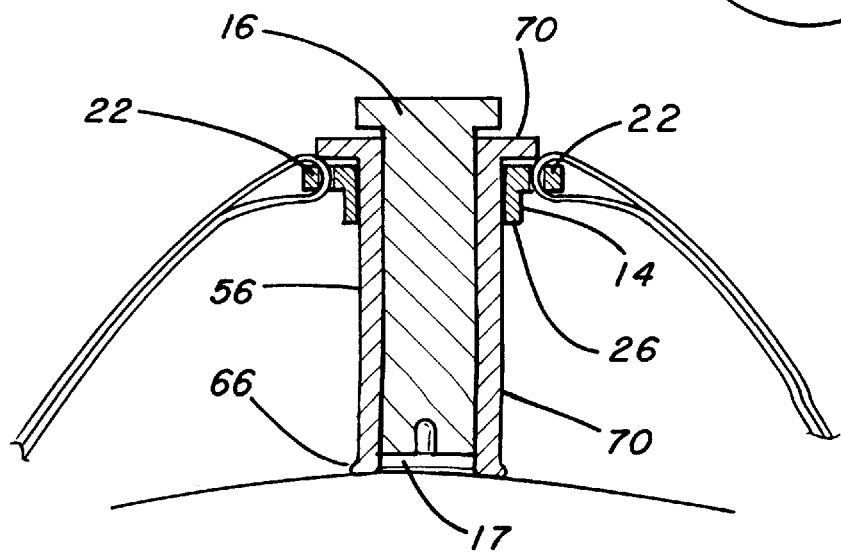
FIG. 6 is a cross-sectional view of an EEG electrode fully inserted in the plunger assembly and electrode locator of FIG. 5.
Figure 7:
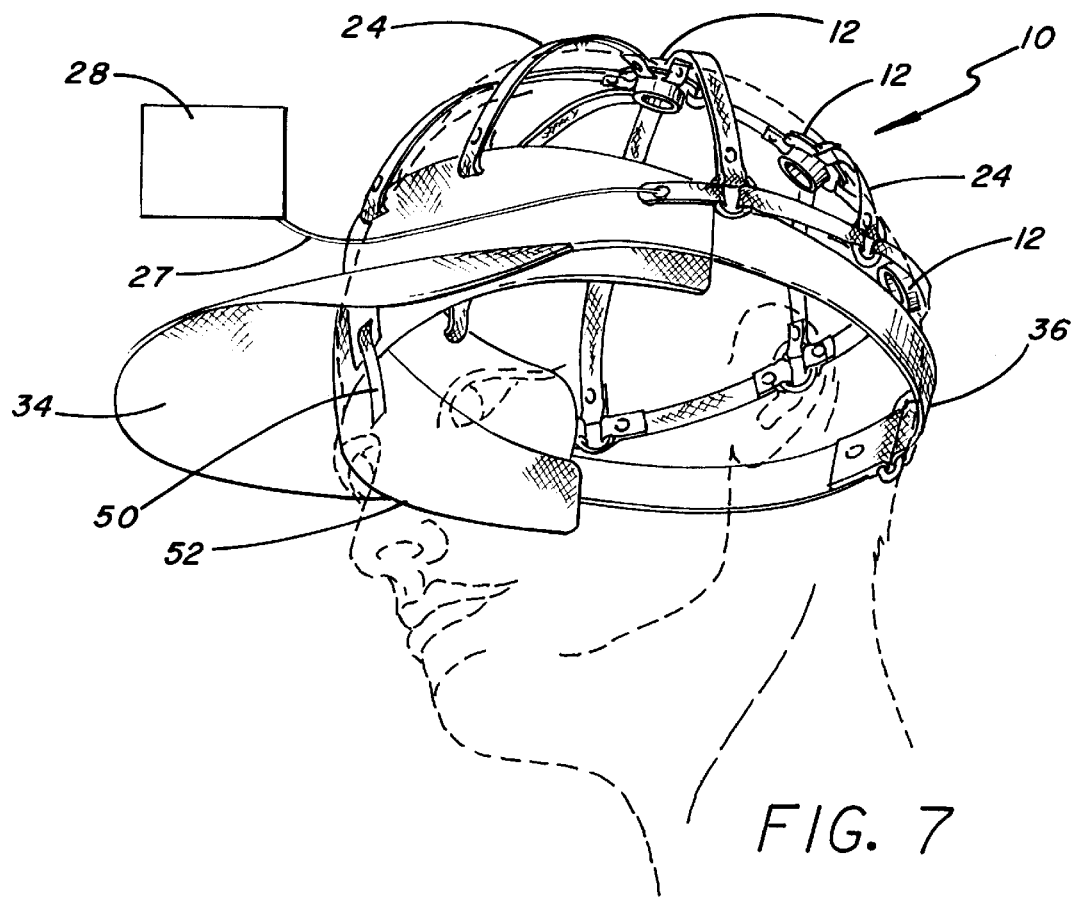
FIG. 7 is a bottom perspective view of an alternate embodiment of the EEG electrode locator headgear of the invention showing a front locator strap.

As is illustrated in the drawings, the invention is embodied in an electroencephalograph (EEG) electrode locator headgear that is portable and comfortable, and allows a user to locate and apply disposable EEG electrodes accurately according to the International 10/20 System without technical assistance, to allow the acquisition of high quality EEG signals. Referring to FIG. 1, the EEG electrode locator headgear or visor 10 includes a plurality of EEG electrode locators 12 for receiving EEG electrodes for accurate positioning on the scalp of a user. The electrode locators each include a hollow tubular base 14 adapted to receive an EEG electrode 16, as illustrated in FIGS. 4 and 6, and has an annular flange 18 extending from an upper edge 20 of the hollow tubular base. A plurality of electrodes are preferably provided, and are adapted to be seated in the corresponding plurality of electrode locators, respectively, by an interference or snap fit with the electrode locators, or by an interference or snap fit with a plunger assembly to be inserted in the electrode locators, as is further explained below. The annular flange typically includes a plurality of slots 22 for receiving a plurality of locator straps 24 that are currently preferably formed of elasticized fabric, in order to assist in biasing the electrode locators toward the scalp of the user, but non-elastic straps, such as fabric or nylon, for example, may also be suitable.

In a presently preferred embodiment, the hollow tubular base of the electrode locator includes an electrical conductor such as a conductor strip 26 adapted to be electrically connected to an EEG electrode, inserted in the hollow tubular base via a plunger assembly, or directly, as will be further explained below. Alternatively, the electrode locator can be made of an electrically conductive metal. The electrical conductor of the hollow tubular base is preferably adapted to be connected, such as by a cable 27 connectable to a connector 29 electrically connected to the electrode locators, to an EEG monitor 28 which is preferably a portable EEG monitor for ambulatory use, such as the portable EEG monitor disclosed in provisional application No. 60/114,528, filed Dec. 31, 1999 which is incorporated by reference herein. In a presently preferred embodiment, three EEG electrode locators are provided that are adapted to be positioned at the top central (Cz), parietal (Pz), and occipital (Oz) positions relative to the scalp of a user, although alternatively additional or fewer electrode locators may also be provided in the headgear for locating EEG electrodes according to the International 10/20 system.

Figure 2:
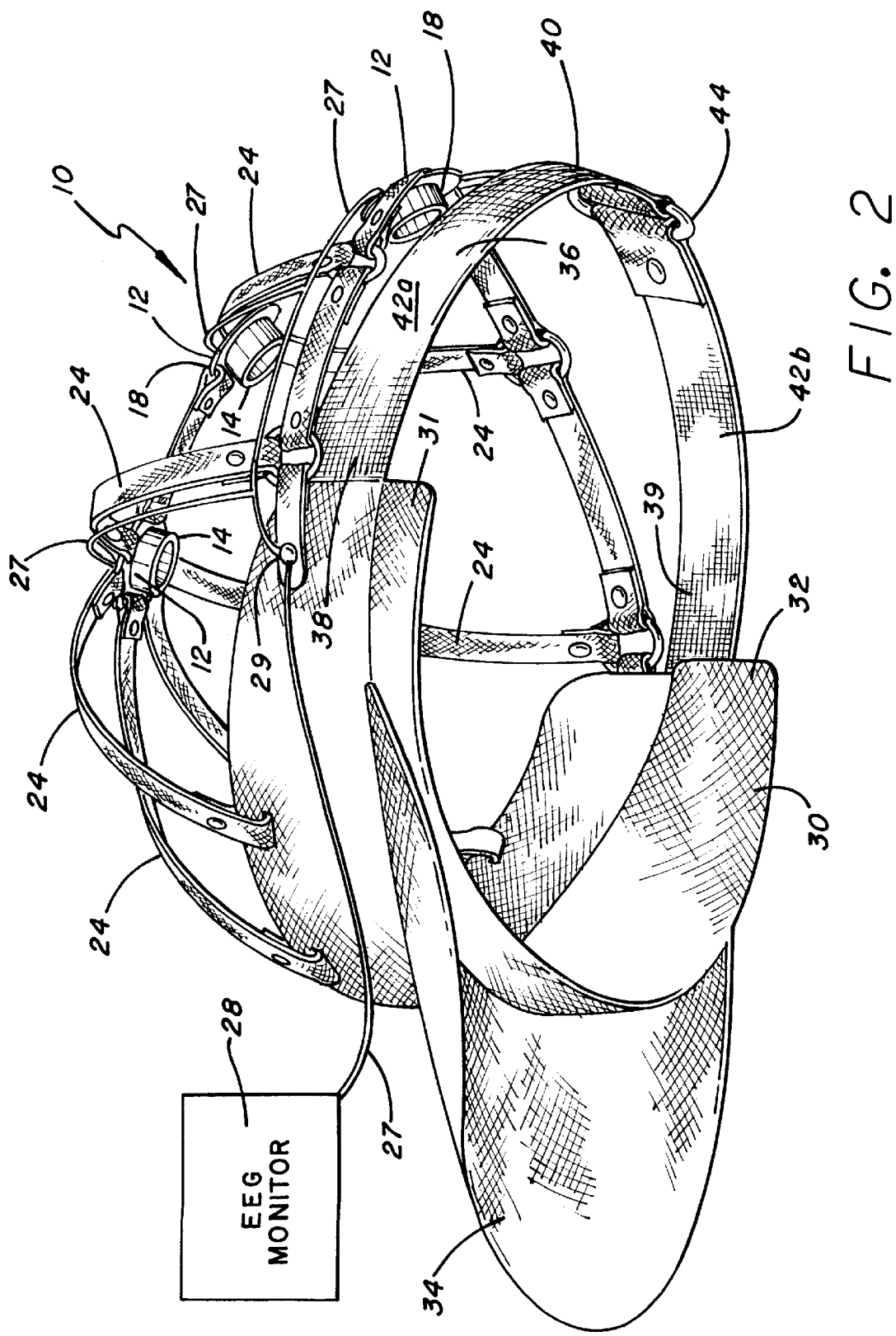
FIG. 2 is a bottom perspective view of the EEG electrode locator headgear of FIG. 1.

In a presently preferred embodiment, as is best seen in FIGS. 1 and 2, the EEG electrode locator headgear advantageously includes a front pad of material 30, having a first end 31 and a second end 32. The front pad of material is adapted to extend across a user's forehead to provide a secure footing for the EEG electrode locator headgear. The front pad of material is preferably made of a non-elastic fabric material, such as cotton or wool, although a variety of synthetic fabrics such as Dacron, for example, may also be suitable. A front visor or bill 34 is preferably attached to the front pad of material. A base strap assembly 36 is also provided, having a first anterior end 38 connected to the first end of the front pad of material, and a second anterior end 39 connected to the second end of the front pad of material, and a posterior end 40. Together, the front pad of material and the base strap assembly are adapted to be secured comfortably around the circumference of a user's head, and the base strap assembly is preferably made to be adjustable. In a presently preferred aspect, the base strap assembly comprises a pair of adjustable elastic edge straps, with the first elastic edge strap 42a being connected at the first anterior end 38, and the second elastic edge strap 42b being connected at the second anterior end 39 of the front pad of material, and adjustably connected together at the posterior end 40. The plurality of locator straps preferably form a network of locator straps connected to the front pad of material, the base strap assembly, and to the plurality of EEG electrode locators for accurately positioning the plurality of EEG electrode locators positioned relative to the scalp of a user. The plurality of locator straps are preferably made of elastic material, such that the locator straps bias the plurality of electrode locators with a biasing pressure toward the user's scalp, and thereby bias the electrodes inserted into the electrode locators toward the user's scalp, to provide a stable electrode-scalp interface capable of producing a high signal quality.

Figure 8:
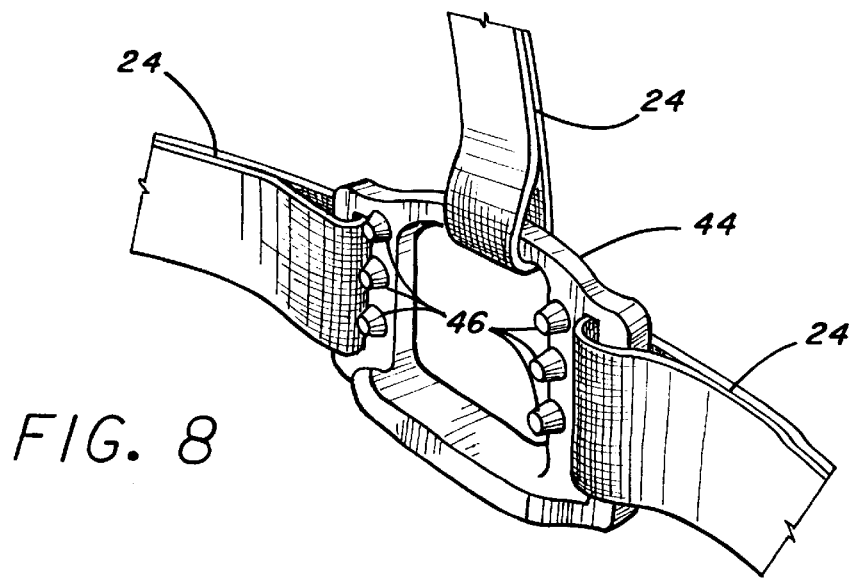
FIG. 8 is a perspective view of an occipital locator of the base strap of the EEG electrode locator headgear of FIG. 1.

In another presently preferred embodiment illustrated in FIG. 8, the base strap assembly includes an occipital locator device 44 adapted to be seated on a region of the user's scalp over the user's occipital bone. The base strap assembly first and second elastic edge straps are thus preferably connected at one end to the front pad of material, and adjustably connected at the other end to the occipital locator device, which is currently preferably a ring, such as a D ring, for example, having a plurality of feet 46 adapted to be positioned over the user's occipital bone.

In another preferred aspect of the EEG electrode locator headgear, an anterior locator strap 50 is connected to the front pad of material, with a free end 52 adapted to be positioned over the user's nasium to confirm accurate placement of the electrode locators.

Figure 3:
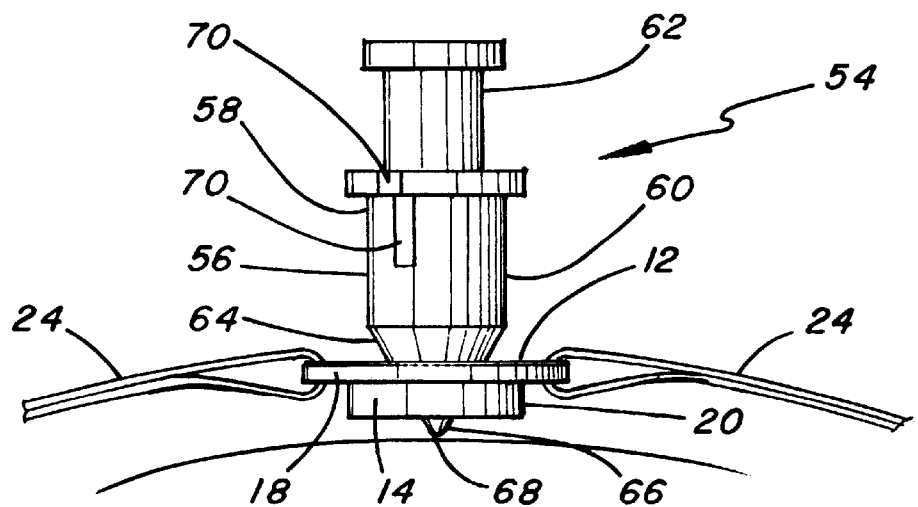
FIG. 3 is a side elevational view of an EEG electrode locator of the EEG electrode locator headgear of FIG. 1, illustrating an EEG electrode, plunger assembly being inserted in the EEG electrode locator.

The EEG electrodes are preferably of the type that are disposable, and as is illustrated in FIGS. 3, 4 and 6, are adapted to be seated in the plurality of electrode locators, respectively. In a presently preferred embodiment, a plunger assembly 54 is also provided that is adapted be used for preparation of the scalp of the user for placement of the disposable electrodes, and is adapted to cooperate with the plurality of electrode locators. In one presently preferred embodiment, the plunger assembly includes a hollow tubular base 56 having an upper portion 58 and a lower portion 60, and a plunger 62 adapted to be received in the hollow tubular base. The upper portion of the plunger assembly tubular base preferably can be seated in the electrode locators by interference or snap fit, although a slot and groove interlocking assembly may alternatively be provided for seating the plunger assembly tubular base in the electrode locators. The lower portion of the hollow tubular base advantageously includes a plurality of flexible, resilient fingers 64 having distal ends 66 biased to come together at a common distal central location 68, and that can be spread by the plunger 62 in order to part the hair of the scalp of the user. Alternatively, as can be seen in FIG. 4, an electrode may also be used for spreading the flexible, resilient fingers of the tubular base of the plunger assembly. In a presently preferred aspect, the spreadable fingers are formed of a plastic, such as a thermoplastic that can be readily molded, for example. The plunger assembly hollow tubular base preferably includes an electrical conductor such as an electrical conductor strip 70 adapted to be electrically connected between an electrode inserted in the hollow tubular base and a corresponding electrical conductor of one of the electrode locators for conducting EEG signals from the electrodes to the EEG monitor 28. The distal flexible, resilient fingers of the plunger hollow tubular base can be spread by insertion of an electrode through the plunger hollow tubular base, so that the plunger assembly can be used to simultaneously part the hair by spreading of the distal fingers of the plunger hollow tubular base, seat the disposable electrode, and optionally also abrade the scalp of the user at the intended location of the electrode, such as by manually twisting the hollow tubular base to rub the distal ends of the distal fingers against the scalp of the user.

Figure 5A:
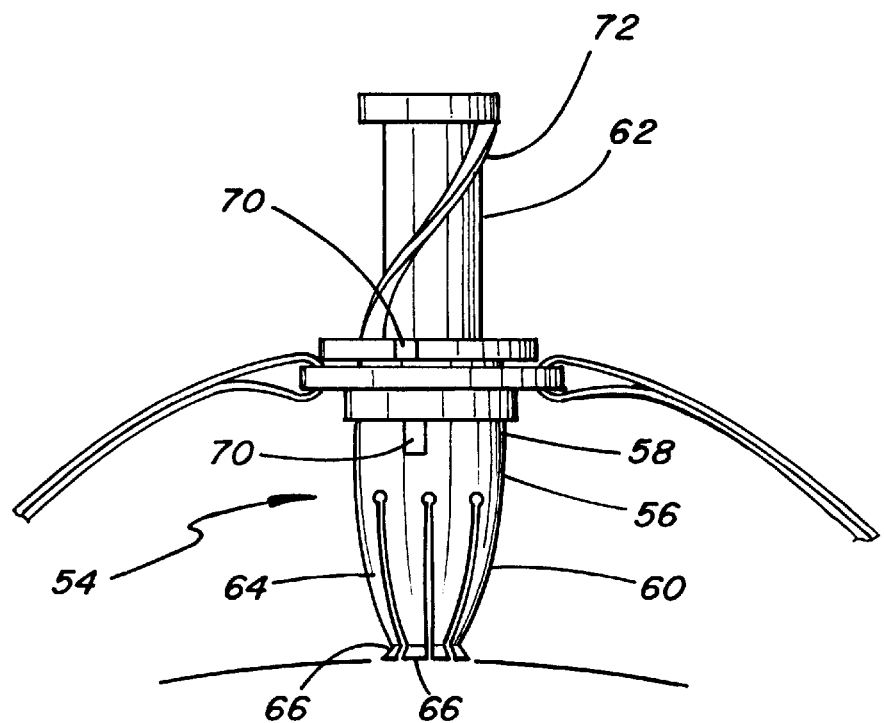
FIG. 5A is a side elevational view of an EEG electrode locator of the EEG electrode locator headgear of FIG. 1, illustrating an alternate plunger assembly being inserted in the EEG electrode locator.
Figure 5B:
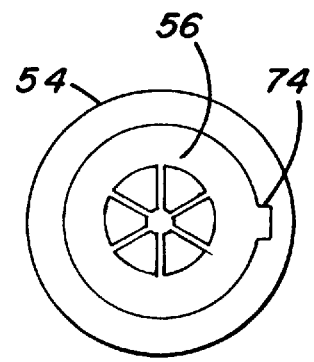
FIG. 5B is a top plan view of the plunger assembly of FIG. 5A.

In another presently preferred alternate embodiment illustrated in FIG. 5, the plunger can be provided with an external helical rib 72, and the hollow tubular base can be provided with a corresponding internal groove 74 for receiving and guiding the external helical rib of the plunger as the plunger is inserted in the hollow tubular base of the plunger assembly, to provide a predetermined turning and torque to the plunger as it is inserted. As is illustrated in FIG. 6, once the plunger has been utilized to spread the fingers of the plunger assembly to part the hair of the scalp of the user, and the scalp has otherwise been prepared as needed, the EEG electrode can be inserted in the electrode locator.

It should be understood that the individual EEG electrodes can alternatively be individually or collectively directly connected such as by one or more cables to an EEG signal monitor, and that other conventional modifications may also be suitable. Although the EEG electrode locator headgear of the invention is advantageously adapted to be usable without a chin strap by an adult user, it should be appreciated that the EEG electrode locator headgear of the invention could also be adapted to include a chin strap for use by children or to meet the special requirements of an individual user. In addition, although the present invention contemplates the location of disposable EEG electrodes in individual EEG electrode locators, it should be appreciated that combined EEG electrode and locator assemblies, such as active, amplified electrodes, for example, may be incorporated into the headgear of the locations of the EEG electrode locators, in the same or a similar manner. Alternatively, active electrodes or preamplifiers could be incorporated into the plunger or connected to the electrical conductor of the electrode locator. It will thus be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An electroencephalograph (EEG) electrode locator headgear, comprising:

a plurality of EEG electrode locators adapted to receive EEG electrodes;

a front pad of material having first and second ends, said front pad of material being adapted to extend across a user's forehead;

a base strap assembly having a first end connected to said first end of said front pad of material, and a second end connected to said second end of said front pad of material, said front pad of material and said base strap assembly being adapted to be secured comfortably around the circumference of a user's head; and a plurality of locator straps connected to said front pad of material, said base strap assembly, and to said plurality of EEG electrode locators for accurately positioning said plurality of EEG electrode locators positioned at predetermined positions relative to the scalp of a user.

2. The EEG electrode locator headgear of claim 1, wherein said plurality of EEG electrode locators each comprise a hollow tubular base adapted to receive an EEG electrode, and an annular flange extending from an upper edge of said hollow tubular base, said annular flange including a plurality of slots for receiving a plurality of said locator straps.

3. The EEG electrode locator headgear of claim 2, wherein said hollow tubular base comprises an electrical conductor adapted to be electrically connected to an EEG electrode inserted in said hollow tubular base.

4. The EEG electrode locator headgear of claim 3, further including electrical conductors electrically connected to said electrical conductors of said hollow tubular bases and adapted to be connected to an EEG monitor.

5. The EEG electrode locator headgear of claim 1, wherein said plurality of EEG electrode locators comprise three EEG electrode locators adapted to be positioned at central (Cz), parietal (Pz), and occipital (Oz) positions relative to the scalp of a user.

6. The EEG electrode locator headgear of claim 1, wherein said base strap assembly is adjustable.

7. The EEG electrode locator headgear of claim 1, wherein said base strap assembly further comprises an occipital locator device adapted to be seated on a region of the user's scalp over the user's occipital bone, said base strap assembly comprising first and second elastic edge straps connected at one end to said front pad of material, and adjustably connected at the other end to said occipital locator device.

8. The EEG electrode locator headgear of claim 7, wherein said occipital locator device comprises a ring having a plurality of feet adapted to be positioned over the user's occipital bone.

9. The EEG electrode locator headgear of claim 7, further comprising anterior locator strap connected to said front pad of material, said anterior locator strap having a free end adapted to be positioned over the user's nasium to confirm accurate placement of the electrode locators.

10. The EEG electrode locator headgear of claim 1, wherein said plurality of locator straps are made of elastic material, such that said locator straps bias said plurality of electrode locators with a biasing pressure toward the user's scalp.

11. The EEG electrode locator headgear of claim 1, further comprising a visor attached to said front pad of material.

12. The EEG electrode locator headgear of claim 1, wherein said base strap assembly comprises a pair of adjustable elastic straps connected at one end to said front pad of material and adjustably connected together at the other end.

13. The EEG electrode locator headgear of claim 1, further comprising a plurality of electrodes adapted to be seated in said plurality of electrode locators, respectively, whereby the electrodes can be inserted into the electrode locators, to provide a stable electrode-scalp interface capable of producing a high signal quality.

14. The EEG electrode locator headgear of claim 1, further comprising a plunger assembly adapted to cooperate with said plurality of electrode locators, including a hollow tubular base having an upper portion and a lower portion, and a plunger adapted to be received in said hollow tubular base, adapted to be inserted in the electrode locators to prepare the scalp of the user and to seat the electrodes.

15. The EEG electrode locator headgear of claim 14, wherein said lower portion of the hollow tubular base includes a plurality of flexible, resilient fingers having distal ends biased to meet at a common distal central location, and that can be spread in order to part the hair of the scalp of the user.

16. The EEG electrode locator headgear of claim 15, wherein said flexible, resilient fingers of the plunger assembly hollow tubular base can be spread by insertion of an electrode through the plunger hollow tubular base, so that the plunger assembly can be used to simultaneously part the hair by spreading of the fingers of the plunger hollow tubular base, seat the disposable electrode, and optionally also abrade the scalp of the user at the intended location of the electrode, such as by manually twisting the hollow tubular base to rub the distal ends of the fingers against the scalp of the user.

17. The EEG electrode locator headgear of claim 15, wherein said plunger is adapted to be inserted in the hollow tubular base of the plunger assembly to spread the flexible, resilient fingers.

18. The EEG electrode locator headgear of claim 17, wherein said plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted.

19. The EEG electrode locator headgear of claim 14, wherein said hollow tubular base includes an electrical conductor adapted to be electrically connected between an electrode inserted in said hollow tubular base and one of said electrode locators for conducting EEG signals from said electrodes to an EEG monitor.

20. An electroencephalograph (EEG) electrode locator visor, comprising:
a plurality of EEG electrode locators adapted to receive EEG electrodes;
a front pad of material having first and second ends, said front pad of material being adapted to extend across a user's forehead;
a visor attached to said front pad of material;
a base strap assembly having a first end connected to said first end of said front pad of material, and a second end connected to said second end of said front pad of material, said front pad of material and said base strap assembly being adapted to be secured comfortably around the circumference of a user's head; and
a plurality of locator straps connected to said front pad of material, said base strap assembly, and to said plurality of EEG electrode locators for accurately positioning said plurality of EEG electrode locators positioned relative to the scalp of a user.

21. The EEG electrode locator headgear of claim 20, wherein said base strap assembly further comprises an occipital locator device adapted to be seated on a region of the user's scalp over the user's occipital bone, said base strap assembly comprising first and second elastic edge straps connected at one end to said front pad of material, and adjustably connected at the other end to said occipital locator device.

22. The EEG electrode locator headgear of claim 20, further comprising anterior locator strap connected to said front pad of material, said anterior locator strap having a free end adapted to be positioned over the user's nasium to confirm accurate placement of the electrode locators.

23. The EEG electrode locator headgear of claim 20, further comprising a plunger assembly adapted to cooperate with said plurality of electrode locators, said plunger assembly including a hollow tubular base having an upper portion and a lower portion.

24. The EEG electrode locator headgear of claim 23, further comprising a plunger adapted to be received in said plunger assembly hollow tubular base, adapted to be inserted in the electrode locators to prepare the scalp of the user and to seat the electrodes.

25. The EEG electrode locator headgear of claim 23, wherein said lower portion of the plunger assembly hollow tubular base includes a plurality of flexible, resilient fingers having distal ends biased to meet at a common distal central location, and that can be spread in order to part the hair of the scalp of the user.

26. The EEG electrode locator headgear of claim 25, wherein said flexible, resilient fingers of the plunger assembly hollow tubular base can be spread by insertion of an electrode through the plunger assembly hollow tubular base, so that the plunger assembly can be used to simultaneously part the hair by spreading of the fingers of the plunger hollow tubular base, seat the disposable electrode, and optionally also abrade the scalp of the user at the intended location of the electrode, such as by manually twisting the hollow tubular base to rub the distal ends of the fingers against the scalp of the user.

27. The EEG electrode locator headgear of claim 25, wherein said plunger is adapted to be inserted in the hollow tubular base of the plunger assembly to spread the flexible, resilient fingers.

28. The EEG electrode locator headgear of claim 27, wherein said plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted.

29. The EEG electrode locator headgear of claim 23, wherein said hollow tubular base includes an electrical conductor adapted to be electrically connected between an electrode inserted in said plunger assembly hollow tubular base and one of said electrode locators for conducting EEG signals from said electrodes to an EEG monitor.

30. An electroencephalograph (EEG) electrode locator headgear, comprising:
a plurality of EEG electrode locators adapted to receive EEG electrodes;
a plunger assembly adapted to cooperate with said plurality of EEG electrode locators, said plunger assembly including a hollow tubular base having an upper portion and a lower portion;
a front pad of material having first and second ends, said front pad of material being adapted to extend across a user's forehead;

a base strap assembly having a first end connected to said first end of said front pad of material, and a second end connected to said second end of said front pad of material, said front pad of material and said base strap assembly being adapted to be secured comfortably around the circumference of a user's head; and a plurality of locator straps connected to said front pad of material, said base strap assembly, and to said plurality of EEG electrode locators for accurately positioning said plurality of EEG electrode locators positioned relative to the scalp of a user.

31. The EEG electrode locator headgear of claim 30, further comprising a plunger adapted to be received in said plunger assembly hollow tubular base, adapted to be inserted in the electrode locators to prepare the scalp of the user and to seat the electrodes.

32. The EEG electrode locator headgear of claim 30, wherein said lower portion of the plunger assembly hollow tubular base includes a plurality of flexible, resilient fingers having distal ends biased to meet at a common distal central location, and that can be spread in order to part the hair of the scalp of the user.

33. The EEG electrode locator headgear of claim 32, wherein said flexible, resilient fingers of the plunger assembly hollow tubular base can be spread by insertion of an electrode through the plunger assembly hollow tubular base, so that the plunger assembly can be used to simultaneously part the hair by spreading of the fingers of the plunger hollow tubular base, seat the disposable electrode, and optionally also abrade the scalp of the user at the intended location of the electrode, such as by manually twisting the hollow tubular base to rub the distal ends of the fingers against the scalp of the user.

34. The EEG electrode locator headgear of claim 32, wherein said plunger is adapted to be inserted in the hollow tubular base of the plunger assembly to spread the flexible, resilient fingers.

35. The EEG electrode locator headgear of claim 34, wherein said plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted.

36. The EEG electrode locator headgear of claim 30, wherein said hollow tubular base includes an electrical conductor adapted to be electrically connected between an electrode inserted in said plunger assembly hollow tubular base and one of said electrode locators for conducting EEG signals from said electrodes to an EEG monitor.

37. An electroencephalograph (EEG) electrode locator headgear, comprising:

a plurality of EEG electrode locators adapted to receive EEG electrodes;

a front pad of material having first and second ends, said front pad of material being adapted to extend across a user's forehead;

a base strap assembly having a first end connected to said first end of said front pad of material, and a second end connected to said second end of said front pad of material, said front pad of material and said base strap assembly being adapted to be secured comfortably around the circumference of a user's head, said base strap assembly including an occipital locator device adapted to be seated on a region of the user's scalp over the user's occipital bone, and said base strap assembly comprising first and second elastic edge straps connected at one end to said front pad of material, and adjustably connected at the other end to said occipital locator device; and a plurality of locator straps connected to said front pad of material, said base strap assembly, and to said plurality of EEG electrode locators for accurately positioning said plurality of EEG electrode locators positioned relative to the scalp of a user.

38. The EEG electrode locator headgear of claim 37, wherein said occipital locator device comprises a ring having a plurality of feet adapted to be positioned over the user's occipital bone.

39. The EEG electrode locator headgear of claim 37, further comprising anterior locator strap connected to said front pad of material, said anterior locator strap having a free end adapted to be positioned over the user's nasium to confirm accurate placement of the electrode locators.

40. An electroencephalograph (EEG) electrode locator headgear, comprising:

a plurality of EEG electrode locators adapted to receive EEG electrodes;

a front pad of material having first and second ends, said front pad of material being adapted to extend across a user's forehead;

a base strap assembly including a pair of adjustable elastic straps each connected at one end to said front pad of material and adjustably connected together at the other end of said adjustable elastic straps, said base strap assembly having a first end connected to said first end of said front pad of material, and a second end connected to said second end of said front pad of material, said front pad of material and said base strap assembly being adapted to be secured comfortably around the circumference of a user's head; and a plurality of locator straps connected to said front pad of material, said base strap assembly, and to said plurality of EEG electrode locators for accurately positioning said plurality of EEG electrode locators positioned relative to the scalp of a user.

41. An electroencephalograph (EEG) electrode locator headgear, comprising:

a plurality of EEG electrode locators adapted to receive EEG electrodes;

a plunger assembly adapted to cooperate with said plurality of EEG electrode locators, said plunger assembly including a hollow tubular base having an upper portion and a lower portion, and a plunger adapted to be received in said hollow tubular base, adapted to be inserted in the electrode locators to prepare the scalp of the user and to seat the electrodes;

a front pad of material having first and second ends, said front pad of material being adapted to extend across a user's forehead;

a base strap assembly having a first end connected to said first end of said front pad of material, and a second end connected to said second end of said front pad of material, said front pad of material and said base strap assembly being adapted to be secured comfortably around the circumference of a user's head; and a plurality of locator straps connected to said front pad of material, said base strap assembly, and to said plurality of EEG electrode locators for accurately positioning said plurality of EEG electrode locators positioned relative to the scalp of a user.

42. The EEG electrode locator headgear of claim 41, wherein said lower portion of the hollow tubular base includes a plurality of flexible, resilient fingers having distal ends biased to meet at a common distal central location, and that can be spread in order to part the hair of the scalp of the user.

43. The EEG electrode locator headgear of claim 42, wherein said flexible, resilient fingers of the plunger assembly hollow tubular base can be spread by insertion of an electrode through the plunger hollow tubular base, so that the plunger assembly can be used to simultaneously part the hair by spreading of the fingers of the plunger hollow tubular base, seat the disposable electrode, and optionally also abrade the scalp of the user at the intended location of the electrode, such as by manually twisting the hollow tubular base to rub the distal ends of the fingers against the scalp of the user.

44. The EEG electrode locator headgear of claim 42, wherein said plunger is adapted to be inserted in the hollow tubular base of the plunger assembly to spread the flexible, resilient fingers.

45. The EEG electrode locator headgear of claim 44, wherein said plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted.

46. The EEG electrode locator headgear of claim 41, wherein said hollow tubular base includes an electrical conductor adapted to be electrically connected between an electrode inserted in said hollow tubular base and one of said electrode locators for conducting EEG signals from said electrodes to an EEG monitor.

* * * * *

UNITED STATES PATENT AND TRADEMARK OFFICE
CERTIFICATE OF CORRECTION

PATENT NO. : 6,161,030
DATED : Dec. 12, 2000
INVENTOR(S) : Daniel J. Levendowski, et al.

It is certified that error appears in the above-identified patent and that said Letters Patent is hereby corrected as shown below:

Column 5, line 62, , change "1999", to read --1998--.

Signed and Sealed this

First Day of May, 2001

Attest:

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,161,030
APPLICATION NO. : 09/245784
DATED : December 12, 2000
INVENTOR(S) : Daniel J. Levendowski et al.

It is certified that error appears in the above-identified patent and that said Letters Patent is hereby corrected as shown below:

Column 1, lines 4-8, delete "The United States Government has rights to this invention pursuant to research supported in whole or in part by NIH contracts R43NS6344 and N43NS72367 and grant R43NS35387 awarded by the National Institute of Neurological Disease and Stroke." and insert instead --This invention was made with government support under NIH contracts N43NS62344 and N43NS72367 and grant R43NS35387 awarded by the National Institute of Neurological Disorders and Stroke. The government has certain rights in the invention.--

Signed and Sealed this

Twenty-second Day of June, 2010

David J. Kappos
*Director of the United States Patent and Trademark Office*